(12) United States Patent
Stössel et al.

(10) Patent No.: US 7,816,531 B2
(45) Date of Patent: Oct. 19, 2010

(54) METAL COMPLEXES

(75) Inventors: Philipp Stössel, Frankfurt (DE); Esther Breuning, Niedernhausen (DE)

(73) Assignee: Merck Patent GmbH, Darmstadt (DE)

( * ) Notice: Subject to any disclaimer, the term of this patent is extended or adjusted under 35 U.S.C. 154(b) by 908 days.

(21) Appl. No.: 11/632,619

(22) PCT Filed: Jul. 14, 2005

(86) PCT No.: PCT/EP2005/007672

§ 371 (c)(1),
(2), (4) Date: Jan. 16, 2007

(87) PCT Pub. No.: WO2006/008069

PCT Pub. Date: Jan. 26, 2006

(65) Prior Publication Data

US 2008/0027220 A1    Jan. 31, 2008

(30) Foreign Application Priority Data

Jul. 16, 2004   (DE)   ........................ 10 2004 034 517

(51) Int. Cl.
*C07F 15/00*   (2006.01)
*C07F 5/02*   (2006.01)
*H01L 51/40*   (2006.01)

(52) U.S. Cl. ..................... 546/6; 546/2; 546/4; 546/13; 548/101; 548/110; 548/402; 548/405; 556/7; 556/9; 556/27; 556/136; 556/137; 438/99; 257/40

(58) Field of Classification Search ..................... 546/2, 546/4, 6, 13; 548/101, 110, 402, 405; 556/7, 556/9, 27, 136, 137; 257/40; 428/99

See application file for complete search history.

(56) References Cited

U.S. PATENT DOCUMENTS

| | | | |
|---|---|---|---|
| 4,539,507 A | 9/1985 | VanSlyke et al. |
| 5,151,629 A | 9/1992 | VanSlyke |
| 5,621,131 A | 4/1997 | Kreuder et al. |
| 6,653,438 B1 | 11/2003 | Spreitzer et al. |
| 6,753,156 B1 | 6/2004 | Mathis et al. |
| 6,838,818 B2 | 1/2005 | Furugori et al. |
| 7,084,273 B2 | 8/2006 | Stössel et al. |
| 7,147,935 B2 | 12/2006 | Kamatani et al. |
| 2003/0068526 A1 | 4/2003 | Kamatani et al. |
| 2004/0086742 A1 | 5/2004 | Ma et al. |
| 2006/0142552 A1 | 6/2006 | Bach et al. |
| 2006/0142604 A1 | 6/2006 | Bach et al. |
| 2006/0149022 A1 | 7/2006 | Parham et al. |
| 2006/0284140 A1 | 12/2006 | Breuning et al. |
| 2007/0060736 A1 | 3/2007 | Becker et al. |
| 2007/0249834 A1 | 10/2007 | Stossel et al. |

FOREIGN PATENT DOCUMENTS

| | | |
|---|---|---|
| DE | 102004003008 A1 | 10/2005 |
| EP | 0321353 A1 | 6/1989 |
| EP | 707020 A2 | 4/1996 |
| EP | 842208 | 5/1998 |
| EP | 894107 | 2/1999 |
| EP | 1028136 A2 | 8/2000 |
| WO | WO-9218552 A1 | 10/1992 |
| WO | WO-0022026 A1 | 4/2000 |
| WO | WO-0244189 A1 | 6/2002 |
| WO | WO-02060910 A1 | 8/2002 |
| WO | WO-02104080 A1 | 12/2002 |
| WO | WO-03/093283 A1 | 11/2003 |
| WO | WO-2004041901 A1 | 5/2004 |
| WO | WO-2004070772 A2 | 8/2004 |
| WO | WO-2004085449 A1 | 10/2004 |
| WO | WO-2004/113412 A2 | 12/2004 |
| WO | WO-2004108738 A1 | 12/2004 |
| WO | WO-2004113468 A1 | 12/2004 |
| WO | WO-2005014689 A2 | 2/2005 |
| WO | WO-2005/113563 A1 | 12/2005 |

OTHER PUBLICATIONS

Galaup et al., Helvetica Chimica Acta, vol. 82, No. 4, pp. 543-560 (1999).*
Slugovc, C., et al., Generation of Heteroatom-Substituted Carbene Complexes of Iridium by Double C-H Activation of Ether and Amine Substrates, Angew. Chem. Int. Ed., 2000, vol. 39, No. 12, 2158-2160.
Slugovc, C., et al., "Investigation of the C-H Activation Potential of [Hydrotris(1$H$-pyrazolato-$\kappa N^1$)borato(1-)]iridium (IrTp$^x$) Fragments Featuring Aromatic Substituents x at the 3-Position of the Pyrazole Rings" Helvetica Chimica Acta, 2001, vol. 84, pp. 2868-2883.
Piguet, C., et al., "Tridentate Binding Units as Structural Patterns for the Design of Nine-Coordinate Lanthanide Building Blocks with Predetermined Properties", Journal of Alloys and Compounds, 2000, vol. 303-304, pp. 94-103.
Lehn, J-M., et al., "Synthesis of Macrobicyclic Cryptates Incorporating Bithiazole, Bisimidazole and Bipyrimidine Binding Subunits", Tetrahedron Letters, 1989, vol. 30, No, 17, pp. 2209-2212.
Alpha, B., et al., "116. Synthesis and Characterisation of Sodium and Lithium Cryptates of Macrobicyclic Ligands Incorporating Pyridine, Bipyridine, and Biisoquinoline Units", Helvetica Chimica Acta, 1988, vol. 71, 1042-1052.
Reisfeld, R., et al., "Rare Earth Ions, Their Spectroscopy of Cryptates and Related Complexes in Sol-Gel Glasses", Optical Materials, 2003, vol. 24, pp. 1-13.
Seel, C., et al., "Molecules with Large cavities in Supramolecular Chemistry", Angewandte Chemie, 1992, vol. 31, No. 5, pp. 528-548.

* cited by examiner

*Primary Examiner*—Porfirio Nazario Gonzalez
(74) *Attorney, Agent, or Firm*—Connolly Bove Lodge & Hutz LLP

(57) ABSTRACT

The invention relates to novel metal complexes. Said compounds can be used as functional materials in a series of different types of applications that can be attributed in the broadest sense to the electronics industry The inventive compounds are defined by formula (1).

30 Claims, No Drawings

METAL COMPLEXES

RELATED APPLICATIONS

This application is a national stage application (under U.S.C. 371) of PCT/EP2005/007672 filed Jul. 14, 2005, which claims benefit of German application 10 2004 034 517.1 filed Jul. 16, 2004.

Organometallic compounds, specifically compounds of the $d^8$ metals, will in the near future be used as functional materials in a number of different applications which can be ascribed to the electronics industry in the broadest sense. In the case of organic electroluminescent devices based on organic components and organic light-emitting diodes (OLEDs) (for example U.S. Pat. Nos. 4,539,507, 5,151,629), the market introduction has already taken place, as confirmed by the car radios from Pioneer and the mobile telephones from Pioneer and SNMD having an "organic display". Further products of this type are just about to be introduced. Nevertheless, significant improvements are still necessary here in order to make these displays a true competitor to the liquid-crystal displays which currently dominate the market.

A development which has been evident in recent years is the use of organometallic complexes which exhibit phosphorescence instead of fluorescence (M. A. Baldo et al., *Appl. Phys. Lett.* 1999, 75, 4-6). For theoretical spin-statistical reasons, an up to four-fold energy and power efficiency is possible using organometallic compounds as phosphorescence emitters. Whether this development will succeed depends on whether corresponding device compositions which are also able to implement these advantages (triplet emission=phosphorescence compared with singlet emission=fluorescence) in OLEDs are found. The main conditions which may be mentioned here are, in particular, a long operating lifetime and high thermal stability, both during operation and also during vapour deposition. Efficient chemical access to the corresponding organometallic compounds must be possible here. This is of particular interest against the background of the rarity of these metals, in the case of ruthenium, osmium, rhodium, iridium, platinum and gold compounds, in order to facilitate resource-conserving use thereof.

Phosphorescent OLEDs to date exhibit the following weak points, inter alia:
1. The operating lifetime is generally still much too short, which prevents the introduction of phosphorescent OLEDs in high-quality and long-life devices.
2. Many of the known metal complexes have low thermal stability, as shown by our own experiments with metal complexes, which are described, for example, in WO 02/104080, in WO 02/44189 and in US 2003/0068526. The deficient thermal stability inevitably results in the liberation of organic pyrolysis products during vacuum deposition of the complexes, which, in some cases even in small amounts, considerably shorten the operating lifetime of the OLEDs. In particular, however, also during purification of the metal complexes by sublimation and during vapour deposition by vacuum processes, it would be desirable to have available complexes which are significantly more temperature-stable since decomposition results in large losses of the complexes.
3. In particular, the stability of metal complexes which, in addition to ligands of the phenylpyridine type, also contain further ligands which have no metal-carbon bond (for example acetylacetonate) is hitherto still inadequate since these ligands are generally bonded to the central metal atom in an excessively labile manner, as shown by our experiments on complexes of this type, as described, for example, in US 2004/0086742.

In particular, simultaneous improvement in the lifetime and the thermal stability of the complexes would be advantageous.

There is therefore a demand for alternative compounds which do not have the above-mentioned weak points, but are at least equivalent to the known metal complexes in relation to efficiency and emission colour.

Surprisingly, it has now been found that metal complexes of polypodal ligands and cryptates exhibit excellent properties on use in OLEDs, in particular as triplet emitters.

The present invention relates to these compounds, which are distinguished by the following improvements over the prior art:
1. The compounds according to the invention—in contrast to many known metal complexes which undergo partial or complete pyrolytic decomposition on sublimation (for example as described in WO 02/44189 and US 2003/0068526)—have high thermal stability. On use in corresponding devices, this stability results in a significant increase in the operating lifetime and furthermore facilitates straightforward application by vacuum methods.
2. The compounds according to the invention—employed as electroluminescent material in pure form or as dopant in combination with a matrix material—result in high efficiencies in OLEDs, where the electroluminescent devices are distinguished by steep current/voltage curves and in particular by a long operating lifetime.
3. The compounds according to the invention in some cases have excellent solubility in organic solvents. These materials can thus be purified more easily and can also be processed from solution by coating or printing techniques. This property is also advantageous in the case of conventional processing by evaporation since cleaning of the plants and the shadow masks employed is thus considerably simplified.

The class of the metal complexes of polypodal ligands and cryptates described in greater detail below and the use thereof as functional materials in opto-electronic devices is novel; however, the efficient preparation and availability thereof as pure substance is of major importance for this purpose.

The present invention thus relates to metal complexes of the formula (1)

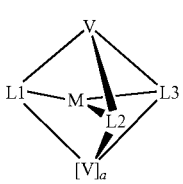

Formula (1)

containing at least one metal M, coordinated to a polypodal ligand L of the formula (2)

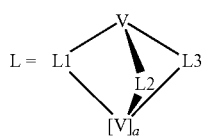

Formula (2)

where V is a bridging unit, containing 1 to 80 atoms from the third, fourth, fifth and/or sixth main group, which covalently bonds the three part-ligands L1, L2 and L3 to one another, and where the index a is equal to 0 or 1, where, in the case a=0, the bridging unit V is omitted;

part-ligand 1 here conforms to the formula (3)

$$L1 = \begin{matrix} Cy1 \\ | \\ Cy2 \end{matrix} \qquad \text{Formula (3)}$$

where Cy1 and Cy2 are substituted or unsubstituted cyclic groups, each of which contains at least one donor atom or C atom in the ring or bonded exocyclically via which the cyclic group is bonded to the metal; the groups Cy1 and Cy2 are bonded to one another via a covalent bond or a common edge and may additionally be linked to one another via substituents and thus form a polycyclic, aliphatic or aromatic ring system;

part-ligand L2 is a donor ligand, containing one or more donor atoms and 2 to 40 C atoms, with the proviso that part-ligand L2 is not built up from two rings or part-rings which are both bonded to the metal directly or via exocyclically bonded donor atoms;

part-ligand L3 is identical to or different from part-ligand L1 or part-ligand L2.

For the purposes of this invention, a donor atom is taken to mean an atom which has at least one free electron pair and which is thus capable of bonding to a metal atom, such as, for example, O, S, N or P. For the purposes of this invention, a donor group or donor ligand is taken to mean a chemical group which has at least one donor atom of this type and is thus able to bond to a metal atom.

The metal complexes of the formula (1) can be complexes of polypodal ligands or cryptates depending on whether one bridging unit V (i.e. a=0) or two bridging units V (i.e. a=1) are present. For the purposes of this invention, a cryptate is taken to mean a compound between a cryptand and a metal ion in which the metal ion is surrounded three-dimensionally by the bridges of the complex-forming cryptand. For the purposes of this invention, a cryptand is taken to mean a macropolycyclic ligand, in particular a ligand in which two bridgehead atoms or bridgehead groups are connected by three bridges, each of which is capable of coordinating to a metal atom.

The cyclic groups Cy1 and Cy2, which may be homocycles or heterocycles, may be saturated, unsaturated or aromatic. The groups are preferably aromatic.

The rings Cy1 and Cy2 of part-ligand L1 can be linked to one another via a single bond. In addition, the part homo- or heterocycles Cy1 and Cy2 can be linked via a common edge. Furthermore, besides the linking via a single bond or a common edge, they can be linked to one another via substituents on rings Cy1 and Cy2 or the part-rings and thus form a polycyclic, aromatic or aliphatic ring system. The main linking possibilities are shown by way of example here with reference to the example of a benzene ring (Cy1) and a pyridine ring (Cy2), without thereby wishing to restrict the variety of all possible links:

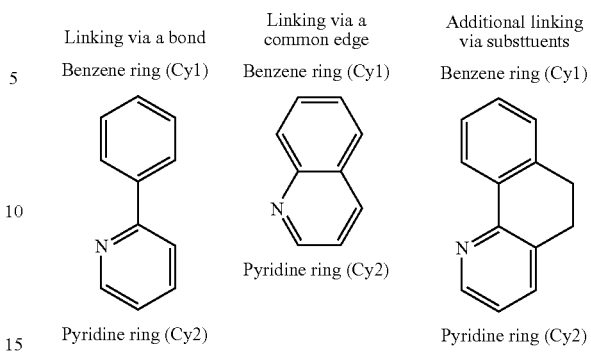

Preference is given to compounds of the formula (1) according to the invention, characterised in that they are not charged, i.e. are electrically neutral. This is achieved in a simple manner in that the charge of part-ligands L1, L2 and L3 and of the bridging units V is selected in such a way that it compensates for the charge of the complexed metal ion.

Preference is furthermore given to compounds of the formula (1) according to the invention, characterised in that the sum of the valence electrons around the metal atom is 18. This preference is due to the particular stability of these metal complexes (see, for example, Elschenbroich, Salzer, *Organometallchemie [Organometallic Chemistry]*, Teubner Studienbücher, Stuttgart 1993).

Preference is furthermore given to compounds of the formula (1) according to the invention, characterised in that Cy1 is not equal to Cy2. It is preferred here for one of the two rings to be bonded via a metal-carbon bond and the other via a donor atom other than carbon.

Preference is given to compounds of the formula (1) according to the invention, characterised in that the bridging unit V has 1 to 80 atoms from main group 3, 4, 5 and/or 6 (IUPAC group 13, 14, 15 or 16) or a 3- to 6-membered homo- or hetero-cycle. These form the skeleton of the bridging unit. The bridging unit V may also have an asymmetrical structure, i.e. the linking of V to L1, L2 and L3 does not have to be identical.

The bridging unit V can be neutral, mononegatively charged or monopositively charged. The charge of V here is preferably selected in such a way that a neutral complex is formed. Thus, for example, one or two neutral bridging units V are preferred in the case of a trivalent metal ion $M^{3+}$ and three mononegative part-ligands L1, L2 and L3. Furthermore, a mononegative bridging unit V and optionally a further neutral unit V is preferred in the case of a tetravalent metal ion $M^{4+}$ and three mononegative part-ligands L1, L2 and L3. Furthermore, two mononegative bridging units V are preferred in the case of a pentavalent metal ion $M^{5+}$ and three mononegative part-ligands L1, L2 and L3. Furthermore, a monopositive bridging unit V and optionally a further neutral unit V is preferred in the case of a divalent metal ion $M^{2+}$ and three mononegative part-ligands L1, L2 and L3. Furthermore, two monopositive bridging units V are preferred in the case of a monovalent metal ion $M^+$ and three mononegative part-ligands L1, L2 and L3.

Preference is furthermore given to compounds of the formula (1) according to the invention, characterised in that part-ligand L2, which contains one or more donor atoms, is a bidentate-chelating part-ligand having two donor atoms.

Preference is again furthermore given to compounds of the formula (1) according to the invention, characterised in that the ligand L of the formula (4) has two part-ligands of type L1 and one bidentate-chelating part-ligand of type L2:

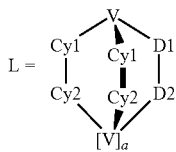

Formula (4)

where the symbols D1 and D2, in each case identically or differently, stand for donor groups, each containing one donor atom; the other symbols and indices used have the meanings mentioned above.

Particular preference is given to compounds of the formula (1) according to the invention, characterised in that L3=L1.

Preferred polypodal metal complexes are selected from the group of the complexes containing part-structures of the formulae (5) to (16), which are explained in greater detail below.

Preference is given to metal complexes of the formula (1) whose part-ligand L1 together with the metal M and the bridging unit V has a part-structure of the formulae (5) to (16):

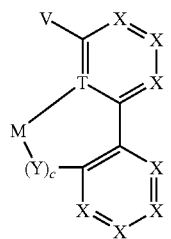

Formula (5)

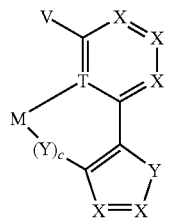

Formula (6)

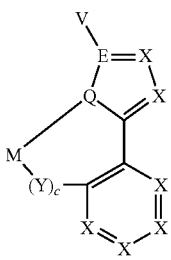

Formula (7)

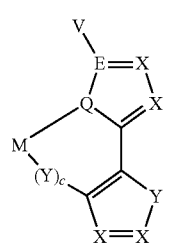

Formula (8)

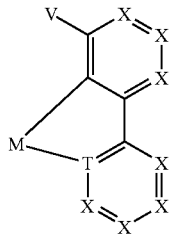

Formula (9)

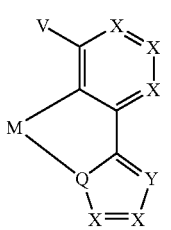

Formula (10)

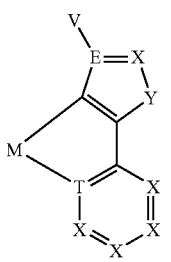

Formula (11)

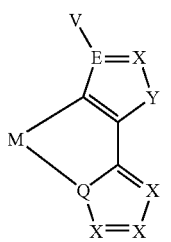

Formula (12)

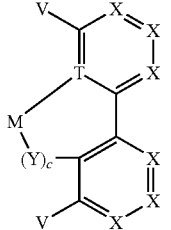

Formula (13)

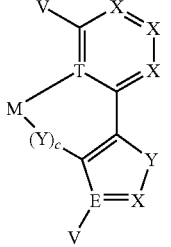

Formula (14)

-continued

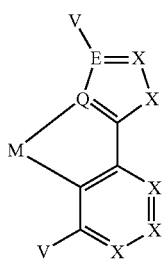

Formula (15)

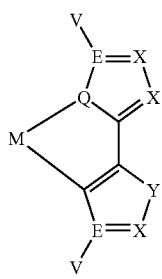

Formula (16)

where the symbols and indices have the following meaning:

M is, identically or differently on each occurrence, a transition metal;

E is, identically or differently on each occurrence, C, N or P;

Q is, identically or differently on each occurrence, O, S, Se, Je or N;

T is, identically or differently on each occurrence, N, P or C;

X is, identically or differently on each occurrence, CR, N or P;

Y is, identically or differently on each occurrence, $NR^1$, O, S, Se, Te, SO, SeO, TeO, $SO_2$, $SeO_2$, $TeO_2$, $R^1SO$, $R^1SeO$, $R^1TeO$, $R^1SO_2$, $R^1SeO_2$, $R^1TeO_2$, $R^1PO$ or $(R^1)_2PO$;

V is, identically or differently on each occurrence, B, BR⁻, $B(CR_2)_3$, $RB(CR_2)_3^-$, $B(O)_3$, $RB(O)_3^-$, $B(CR_2CR_2)_3$, $RB(CR_2CR_2)_3^-$, $B(CR_2O)_3$, $RB(CR_2O)_3^-$, $B(OCR_2)_3$, $RB(OCR_2)_3^-$, $Al(O)_3$, $RAl(O)_3^-$, $Al(OCR_2)_3$, $RAl(OCR_2)_3^-$, CR, CO⁻, $CN(R^1)_2$, $RC(CR_2)_3$, $RC(O)_3$, $RC(CR_2CR_2)_3$, $RC(CR_2O)_3$, $RC(OCR_2)_3$, $RC(SiR_2)_3$, $RC(SiR_2CR_2)_3$, $RC(CR_2SiR_2)_3$, $RC(SiR_2SiR_2)_3$, SiR, RSi $(CR_2)_3$, $RSi(O)_3$, $RSi(CR_2CR_2)_3$, $RSi(OCR_2)_3$, RSi $(CR_2O)_3$, $RSi(SiR_2)_3$, $RSi(SiR_2CR_2)_3$, $RSi(CR_2SiR_2)_3$, $RSi(SiR_2SiR_2)_3$, N, NO, $NR^+$, $N(CR_2)_3$, $RN(CR_2)_3^+$, $N(C=O)_3$, $N(CR_2CR_2)_3$, $RN(CR_2CR_2)^+$, P, PO, PS, PSe, PTe, $P(O)_3$, $PO(O)_3$, $P(OCR_2)_3$, $PO(OCR_2)_3$, $P(CR_2)_3$, $PO(CR_2)_3$, $P(CR_2CR_2)_3$, $PO(CR_2CR_2)_3$, As, AsO, AsS, AsSe, AsTe, $As(O)_3$, $AsO(O)_3$, $As(OCR_2)_3$, $AsO(OCR_2)_3$, $As(CR_2)_3$, $AsO(CR_2)_3$, $As(CR_2CR_2)_3$, $AsO(CR_2CR_2)_3$, Sb, SbO, SbS, SbSe, SbTe, $Sb(O)_3$, $SbO(O)_3$, $Sb(OCR_2)_3$, $SbO(OCR_2)_3$, $Sb(CR_2)_3$, $SbO(CR_2)_3$, $Sb(CR_2CR_2)_3$, $SbO(CR_2CR_2)_3$, Bi, BiO, BiS, BiSe, BiTe, $Bi(O)_3$, $BiO(O)_3$, $Bi(OCR_2)_3$, $BiO(OCR_2)_3$, $Bi(CR_2)_3$, $BiO(CR_2)_3$, $Bi(CR_2CR_2)_3$, $BiO(CR_2CR_2)_3$, $S^+$, $S(CR_2)_3^+$, $S(CR_2CR_2)_3^+$, $Se^+$, $Se(CR_2)_3^+$, $Se(CR_2CR_2)_3^+$, $Te^+$, $Te(CR_2)_3^+$, $Te(CR_2CR_2)_3^+$ or corresponding asymmetrical analogues;

or a unit of the formula (17) or formula (18)

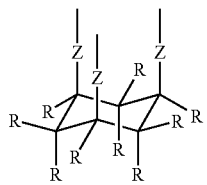

Formula (17)

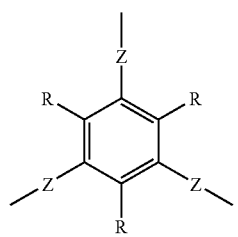

Formula (18)

Z is on each occurrence, identically or differently, a divalent group $CR_2$, NR, O, S, $SiR_2$, PR, $CR_2$—$CR_2$, $CR_2$—NR, $CR_2$—O, $CR_2$—S, $CR_2$—$SiR_2$ or $CR_2$—PR;

R is, identically or differently on each occurrence, H, F, Cl, Br, I, $NO_2$, CN, a straight-chain, branched or cyclic alkyl or alkoxy group having 1 to 20 C atoms, in which one or more non-adjacent $CH_2$ groups may be replaced by —$R^1C$=$CR^1$—, —C≡C—, $Si(R^1)_2$, $Ge(R^1)_2$, $Sn(R^1)_2$, C=O, C=S, C=Se, C=$NR^1$, —O—, —S—, —$NR^1$— or —$CONR^1$— and in which one or more H atoms may be replaced by F, or an aryl, aryloxy or heteroaryl group having 1 to 14 C atoms, which may be substituted by one or more non-aromatic radicals R, or a diarylamino group having 6 to 20 C atoms, which may be substituted by one or more non-aromatic radicals R; a plurality of substituents R here, both on the same ring and also on the two different rings, may together in turn form a further mono- or polycyclic, aliphatic, aromatic and/or benzo-fused ring system;

$R^1$ is, identically or differently on each occurrence, H or an aliphatic or aromatic hydrocarbon radical having 1 to 20 C atoms;

c is, identically or differently on each occurrence, 0 or 1.

The part-structures of the formulae (5) to (16), considered without the metal M and without the bridging unit(s) V, correspond to part-ligand L1 here.

Preference is given to compounds in which M on each occurrence, identically or differently, stands for a transition-metal ion having an atomic number of greater than 38, particularly preferably for tungsten, rhenium, ruthenium, osmium, rhodium, iridium, platinum or gold.

Preference is furthermore given to compounds in which Q on each occurrence, identically or differently, stands for O, S or N, particularly preferably for O or S.

Preference is furthermore given to compounds in which E on each occurrence, identically or differently, stands for C or N, particularly preferably for C.

Preference is furthermore given to compounds in which T on each occurrence, identically or differently, stands for N or P, particularly preferably for N.

Preference is furthermore given to compounds in which X on each occurrence, identically or differently, stands for CR or N.

Preference is furthermore given to compounds in which Y on each occurrence, identically or differently, stands for O, S or $NR^1$.

Preference is furthermore given to compounds in which V on each occurrence, identically or differently, stands for B, BR$^-$, B(CR$_2$)$_3$, RB(CR$_2$)$_3$$^-$, B(O)$_3$, RB(O)$_3$$^-$, B(CR$_2$CR$_2$)$_3$, B(OCR$_2$)$_3$, RB(OCR$_2$)$_3$$^-$, CR, CNR$^1$$_2$, RC(CR$_2$)$_3$, RC(O)$_3$, RC(CR$_2$CR$_2$)$_3$, RC(CR$_2$O)$_3$, RC(OCR$_2$)$_3$, SiR, RSi(CR$_2$)$_3$, RSi(O)$_3$, RSi(CR$_2$CR$_2$)$_3$, RSi(OCR$_2$)$_3$, RSi(CR$_2$O)$_3$, N, NR$^+$, N(CR$_2$)$_3$, RN(CR$_2$)$_3$$^+$, N(C=O)$_3$, N(CR$_2$CR$_2$)$_3$, RN(CR$_2$CR$_2$)$^+$, P, PO, P(O)$_3$, PO(O)$_3$, P(OCR$_2$)$_3$, PO(OCR$_2$)$_3$, S$^+$, S(CR$_2$)$_3$$^+$, S(CR$_2$CR$_2$)$_3$$^+$ or corresponding asymmetrical analogues or a group of the formula (17) or formula (18). V particularly preferably on each occurrence, identically or differently, stands for B(O)$_3$, RB(O)$_3$$^-$, B(OCR$_2$)$_3$, RB(OCR$_2$)$_3$$^-$, RC(CR$_2$CR$_2$)$_3$, RC(CR$_2$O)$_3$, P(O)$_3$, P(OCR$_2$)$_3$, RC(CR$_2$)$_3$, RSi(O)$_3$, N(CR$_2$)$_3$, RN(CR$_2$)$_3$$^+$, N(CR$_2$CR$_2$)$_3$ or corresponding asymmetrical analogues or a group of the formula (17) or formula (18).

Preference is furthermore given to compounds in which Z on each occurrence, identically or differently, stands for a divalent group CR$_2$, NR, O, S, SiR$_2$ or PR, particularly preferably for a divalent group CR$_2$, NR or O.

Preference is furthermore given to compounds in which R on each occurrence, identically or differently, stands for H, F, Cl, Br, I, CN, a straight-chain, branched or cyclic alkyl or alkoxy group having 1 to 6 C atoms or an aryl, aryloxy or heteroaryl group having 3 to 8 C atoms, which may be substituted by one or more non-aromatic radicals R, or a diarylamino group having 8 to 12 C atoms, which may be substituted by one or more non-aromatic radicals R; two or more substituents R here, both on the same ring and also on the two different rings, may together in turn form a further mono- or polycyclic, aliphatic, aromatic and/or benzo-fused ring system.

Preference is furthermore given to compounds in which the index c=0.

The metals here can be in various valences. The above-mentioned metals are preferably in the valences W(II), W(III), W(IV), Re(II), Re(III), Re(IV), Ru(II), Ru(III), Os(II), Os(III), Rh(III), Ir(III), Ir(IV), Pt(IV) and Au(III).

Part-ligand L2 is preferably a bidentate-chelating ligand which has two donor groups D1 and D2, where the corresponding donor atoms are preferably selected from main groups 5 and 6 or represent isonitrile groups; the donor groups D1 and D2 here cannot both represent cyclic systems which are both bonded to the metal. Furthermore, the complexed part-ligand L2 preferably does not have a direct metal-carbon bond. A wide variety of suitable bidentate ligands are known to the person skilled in the art, and many examples are given in Cotton, Wilkinson, *Anorganische Chemie [Inorganic Chemistry]*, 2nd edition, Verlag Chemie, Weinheim, 1970, pp. 917-972.

Particularly preferred donor atoms of donor groups D1 and D2 are nitrogen, phosphorus, oxygen and sulfur.

Preferred nitrogen-containing donor groups are aromatic nitrogen heterocycles, for example pyridine, quinoline, isoquinoline, pyrazine, quinoxaline, pyrimidine, pyridazine, triazine, pyrrole, indole, imidazole, benzimidazole, pyrazole or triazole, aliphatic amines, aliphatic cyclic amines, for example pyrrolidine, piperidine or morpholine, nitriles, amides, imides and imines, each of which may be substituted by groups R or unsubstituted.

Preferred phosphorus-containing donor groups are alkyl-, aryl- or mixed alkylarylphosphines, alkyl-, aryl- or mixed alkylarylphosphine halides, alkyl, aryl or mixed alkyl aryl phosphites or phosphaaromatics, such as, for example, phosphabenzene, each of which may be substituted by groups R or unsubstituted.

Preferred oxygen-containing donor groups are alcohols, alcoholates, open-chain or cyclic ethers, carbonyl groups, phosphine oxide groups, sulfoxide groups, carboxylates, phenols, phenolates, oximes, hydroxamates, β-ketoketonates, β-ketoesters and β-diesters, each of which may be substituted by groups R or unsubstituted, where the last-mentioned groups represent bidentate-chelating ligands.

Preferred sulfur-containing donor groups are aliphatic or aromatic thiols and thiolates, open-chain or cyclic thioethers, thiophene, thiocarbonyl groups, phosphine sulfides and thiocarboxylates, each of which may be substituted by groups R or unsubstituted.

The preferred bidentate-chelating part-ligands L2 can be formed from these donor groups by combining two of these groups, which may be identical or different and may have identical or different donor atoms, but must not represent two cyclic coordinating systems. The part-ligands L2 formed in this way are covalently bonded to the linking unit V and may also be substituted by one or more radicals R.

Examples of part-ligands L2 of this type are substituted or unsubstituted β-ketoketonates, β-ketoesters, β-diesters, carboxylates derived from aminocarboxylic acids, such as, for example, pyridine-2-carboxylic acid, quinoline-2-carboxylic acid, glycine, dimethylglycine, alanine or dimethylaminoalanine, iminoacetoacetonates, hydroxamates, pyridylphosphines, α-phosphinocarboxylates, glycol ethers, ether alcoholates, dialcoholates derived from dialcohols, such as, for example, ethylene glycol or 1,3-propylene glycol, dithiolates derived from dithiols, such as, for example, 1,2-ethylenedithiol or 1,3-propylenedithiol, diamines, such as, for example, ethylenediamine, propylenediamine or cis- or trans-diaminocyclohexane, imines, such as, for example, 2-[1-(phenylimino)ethyl]pyridine, 2-[1-(2-methylphenylimino)ethyl]pyridine, 2-[1-(2,6-di-iso-propylphenylimino)ethyl]pyridine, 2-[1-(methylimino)ethyl]pyridine, 2-[1-(ethylimino)ethyl]pyridine, 2-[1-(iso-propylimino)ethyl]pyridine or 2-[1-(tert-butylimino)ethyl]pyridine, diimines, such as, for example, 1,2-bis(methylimino)-ethane, 1,2-bis(ethylimino)ethane, 1,2-bis(iso-propylimino)ethane, 1,2-bis(tert-butyl-imino)ethane, 2,3-bis(methylimino)butane, 2,3-bis(ethylimino)butane, 2,3-bis(iso-propylimino)butane, 2,3-bis(tert-butylimino)butane, 1,2-bis(phenylimino)ethane, 1,2-bis(2-methylphenylimino)ethane, 1,2-bis(2,6-di-iso-propylphenylimino)ethane, 1,2-bis(2,6-di-tert-butylphenylimino)ethane, 2,3-bis(phenylimino)butane, 2,3-bis(2-methylphenylimino)butane, 2,3-bis(2,6-di-iso-propylphenylimino)butane or 2,3-bis-(2,6-di-tert-butylphenylimino)butane, diphosphines, such as, for example, bis-diphenylphosphinomethane, bisdiphenylphosphinoethane, bis(diphenylphosphino)-propane, bis(dimethylphosphino)methane, bis(dimethylphosphino)ethane, bis(di-methylphosphino)propane, bis(diethylphosphino)methane, bis(diethylphosphino-)ethane, bis(diethylphosphino)propane, bis(di-tert-butylphosphino)methane, bis(di-tert-butylphosphino)ethane, bis(tert-butylphosphino)propane, salicyliminates derived from salicylimines, such as, for example, methylsalicylimine, ethylsalicylimine or phenylsalicylimine, etc.

However, the person skilled in the art can easily, without further inventive step, form further part-ligands L2 from the donor groups mentioned and employ these in the ligands L and the corresponding metal complexes of the formula (1).

The corresponding ligands L of the formula (2), which are valuable intermediates for the synthesis of the complexes according to the invention, are novel and are therefore likewise a subject-matter of the present invention. The preferences described above for complexes of the formula (1) also apply here to the corresponding ligands of the formula (2).

The complexes of the formula (1) according to the invention can in principle be prepared by various processes, but the processes described below have proven particularly suitable.

The present invention therefore furthermore relates to a process for the preparation of the complexes of the formula (1) by reaction of the ligands of the formula (2) or precursors of these ligands with metal alcoholates of the formula (19), with metal ketoketonates of the formula (20) or metal halides of the formula (21)

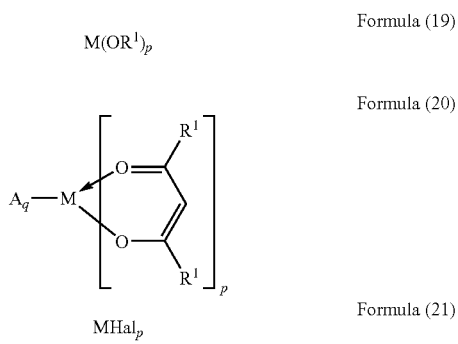

Formula (19)

Formula (20)

Formula (21)

where the following applies to the symbols and indices:

M is on each occurrence, identically or differently, a transition-metal ion;

Hal is on each occurrence, identically or differently, F, Cl, Br or I;

A is on each occurrence, identically or differently, a neutral or monoanionic, monodentate or bidentate ligand, for example a halide or hydroxide;

p is on each occurrence, identically or differently, 1, 2, 3, 4 or 5, where p in formulae (19) and (21) indicates the valence of the metal M;

q is on each occurrence, identically or differently, 0, 1, 2, 3 or 4, preferably 0, 1 or 2;

the compound of the formula (20) here may also be charged and also contain a counterion; the other symbols have the same meaning as indicated above.

The synthesis can be activated, for example, thermally, photochemically or by microwave radiation. The synthesis of tris-ortho-metallated metal complexes is described in general in WO 02/060910, WO 04/085449 and WO 04/108738.

In a preferred synthetic process, the ligand of the formula (2) is reacted with metal compounds, as described by formulae (19), (20) and (21). This synthetic method is shown in scheme 1:

Scheme 1:

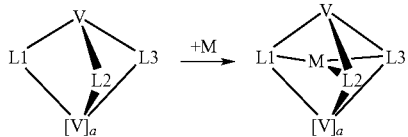

A further preferred synthetic process for the complexes and cryptates according to the invention has proven to be template synthesis, as shown in scheme 2. To this end, metal compounds, as described by the formulae (19), (20) and (21), are reacted with a simple, macrocyclic or polypodal precursor of the ligand, where the ligand precursor differs from the ligand in that it contains no or only one bridging unit V instead of one or two or in that it only contains two of the three part-ligands L1, L2 and L3. In a second synthetic step, the bridging unit V is then introduced in a complex-analogous reaction, i.e. a reaction on the metal complex, or both bridging units V are introduced, or the third part-ligand L1 or L2 or L3 is introduced and linked to the bridging units V. These synthetic methods have the advantage that, due to the fact that the complex formation has already taken place, the three part-ligands L1, L2 and L3 are in a spatially preferred arrangement which facilitates simple ring closure in order to introduce V or in order to link the third part-ligand, which is only possible with greater technical complexity and in worse yields using the uncomplexed part-ligands. These synthetic methods are shown in scheme 2:

Scheme 2:

Synthesis with formation of one bridging unit V:

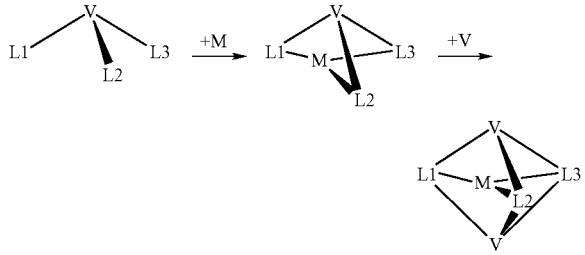

Synthesis with formation of all bridging units V:

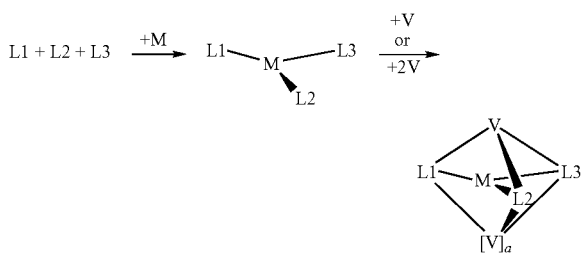

Synthesis with introduction and linking of the third part-ligand:

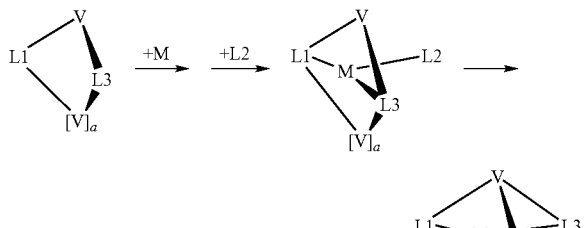

These processes give the complexes easily in high purity, preferably in a purity of >99% according to $^1$H-NMR or HPLC.

The examples of complexes of the formula (1) shown below, inter alia, can be prepared using the synthetic methods explained here.

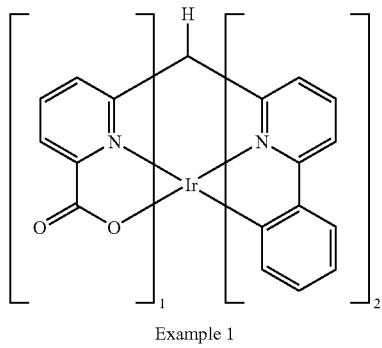
Example 1
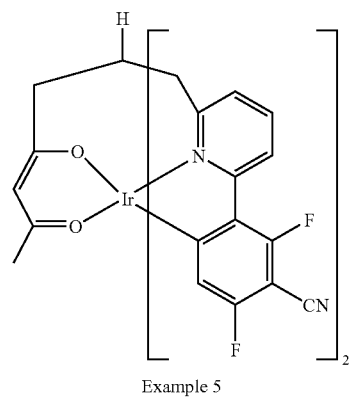
Example 5
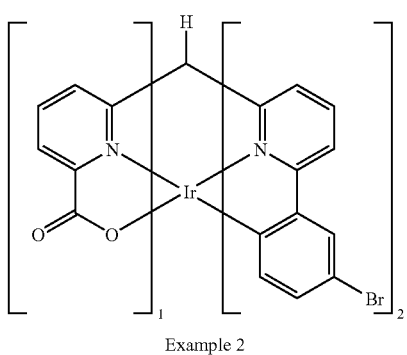
Example 2
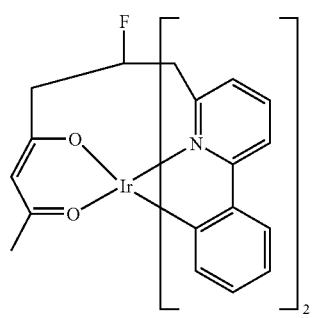
Example 6
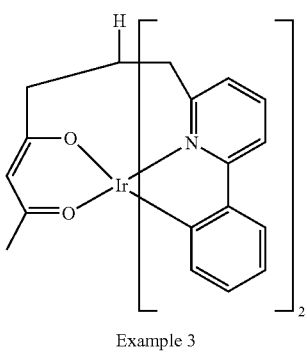
Example 3
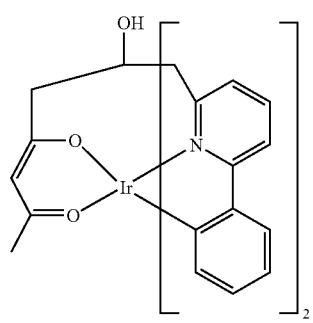
Example 7
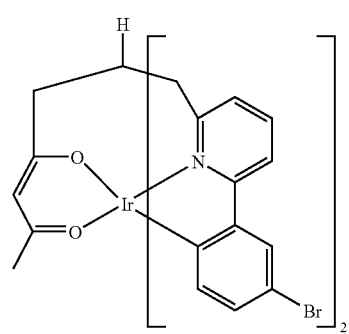
Example 4
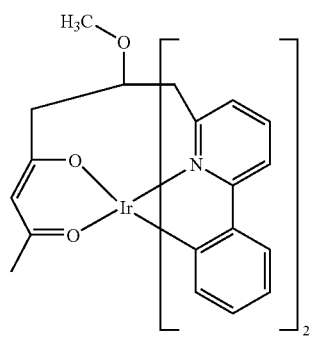
Example 8

-continued
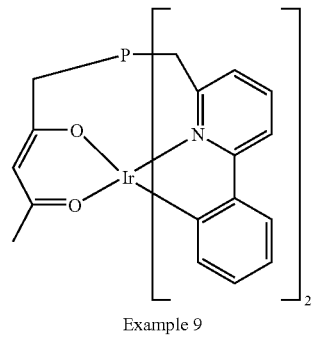
Example 9
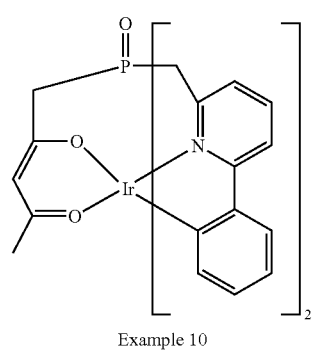
Example 10
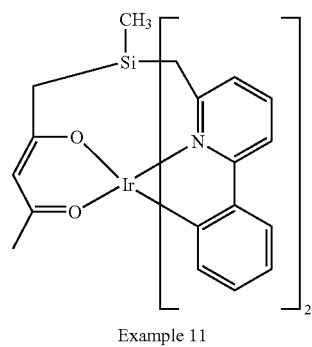
Example 11
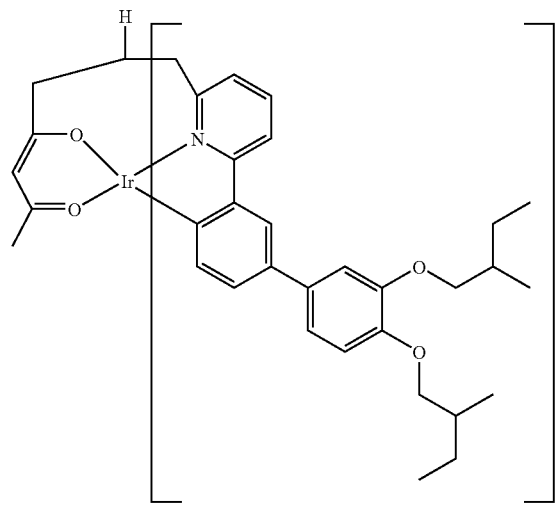
Example 12
-continued
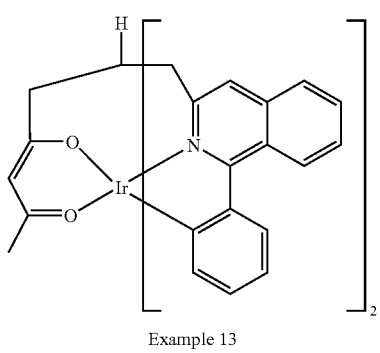
Example 13
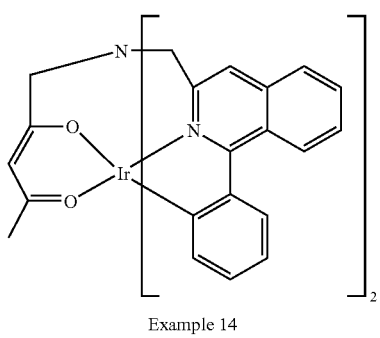
Example 14
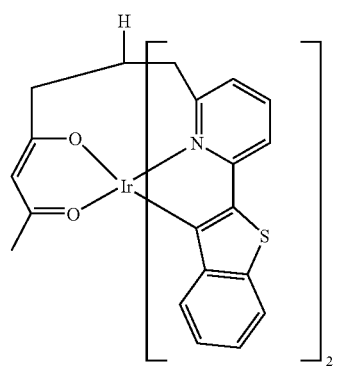
Example 15
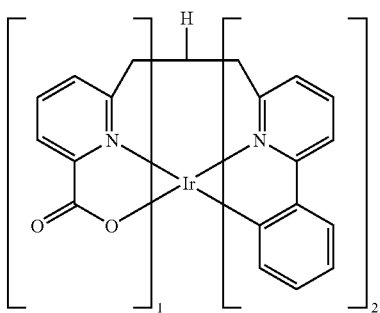
Example 16

-continued
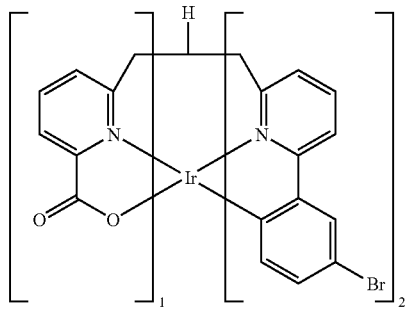
Example 17
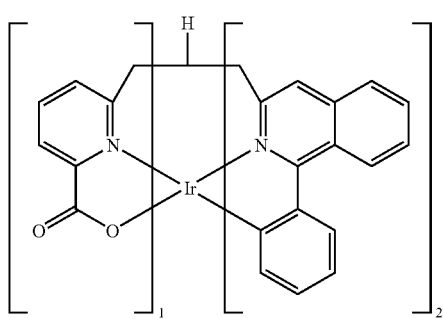
Example 18
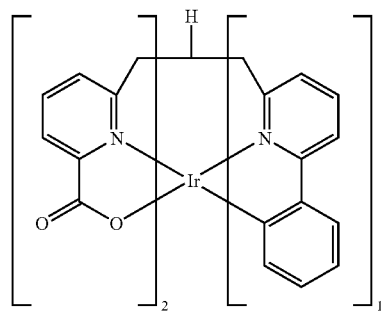
Example 19
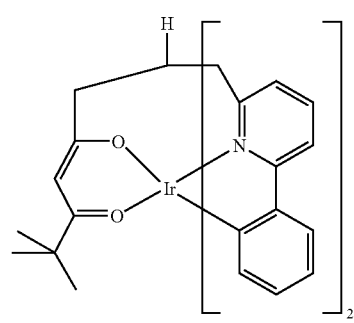
Example 20
-continued
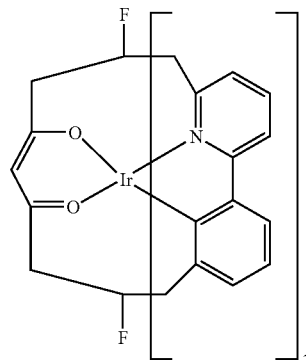
Example 21
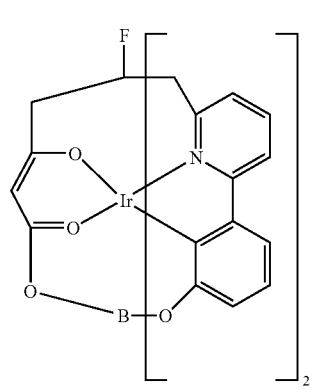
Example 22
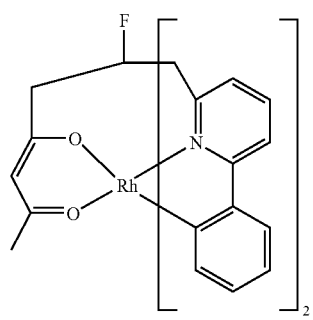
Example 23
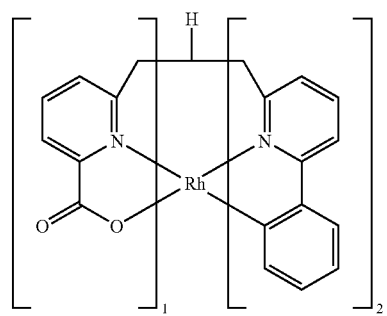
Example 24

-continued
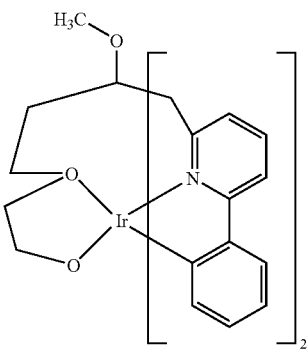
Example 25
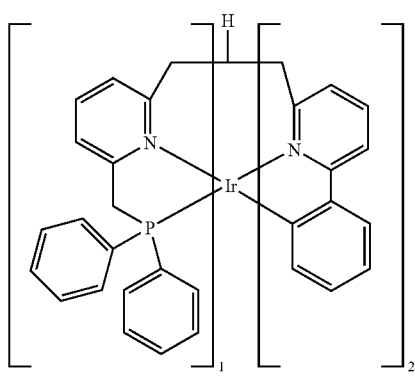
Example 26
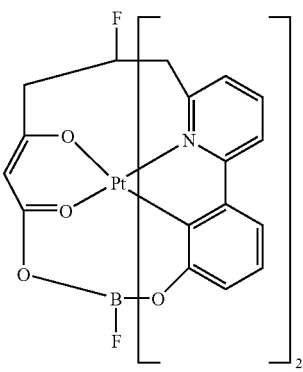
Example 27
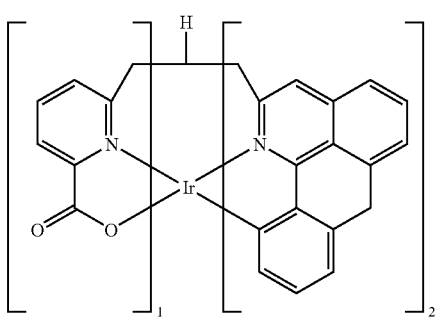
Example 28
-continued
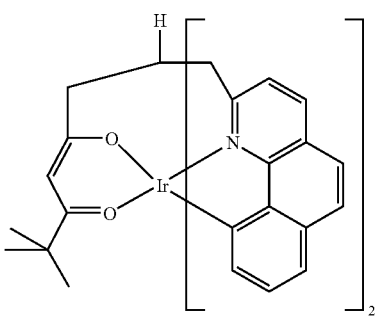
Example 29
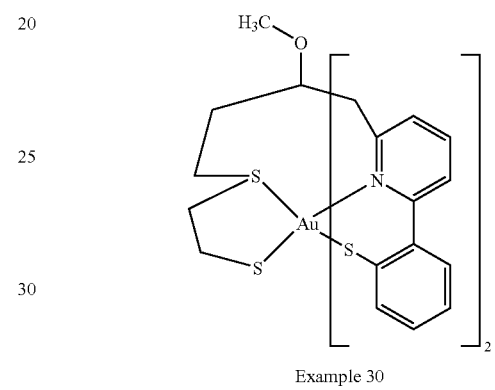
Example 30
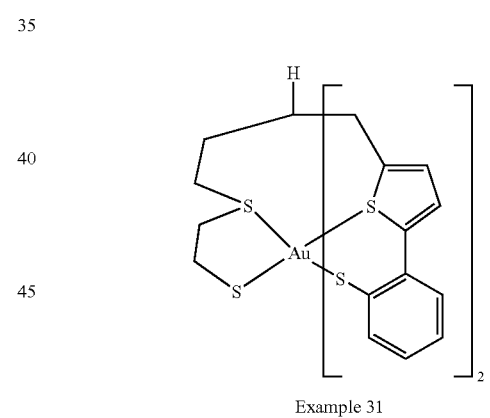
Example 31
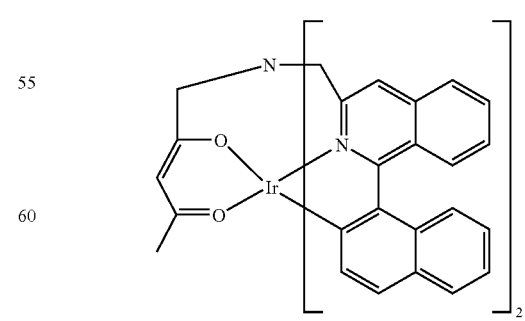
Example 32

-continued
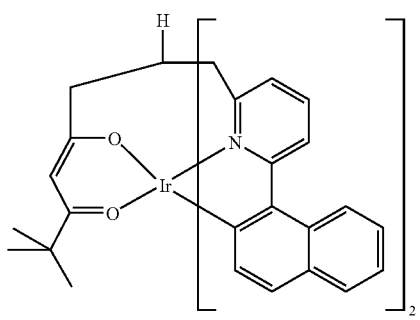
Example 33
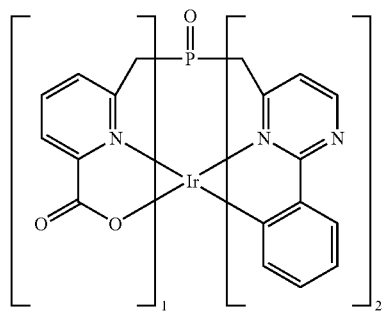
Example 34
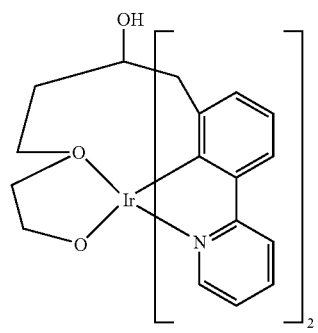
Example 35
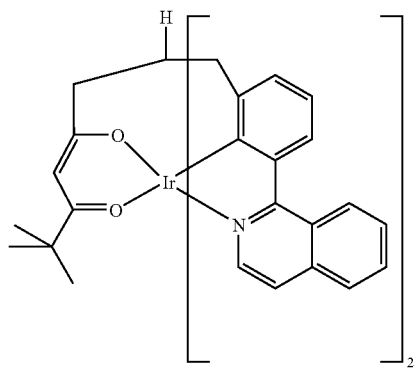
Example 36
-continued
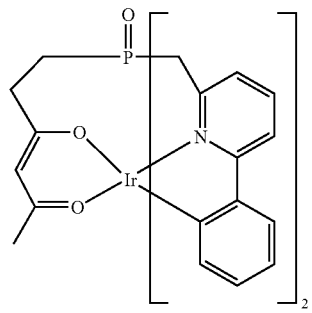
Example 37
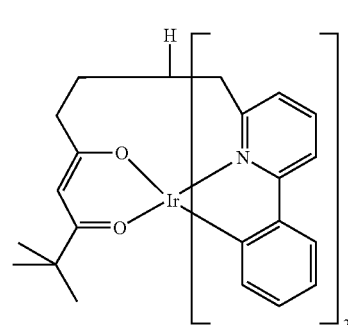
Example 38
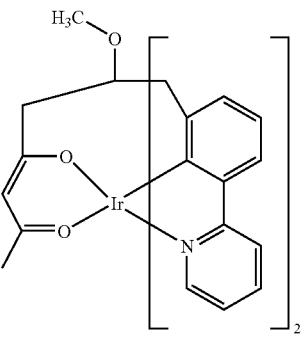
Example 39
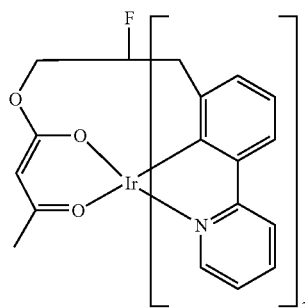
Example 40

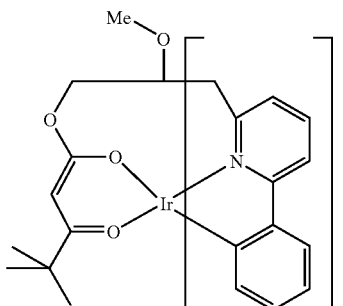

Example 41

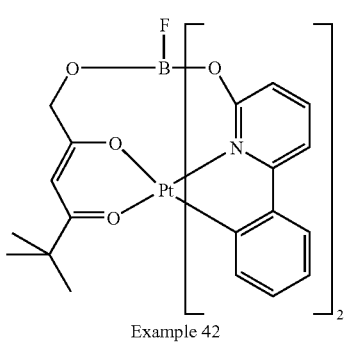

Example 42

The compounds according to the invention described above—for example compounds in accordance with Examples 2 and 4—can be used, for example, as comonomers for the preparation of corresponding conjugated, partially conjugated or non-conjugated polymers or also as the core of dendrimers. The polymerisation here is preferably carried out via the halogen functionality. Thus, they can be polymerised, inter alia, into soluble polyfluorenes (for example as described in EP 842208 or WO 00/22026), polyspirobifluorenes (for example as described in EP 707020 or EP 894107), poly-para-phenylenes (for example as described in WO 92/18552), polycarbazoles (for example as described in WO 04/070772 and WO 04/113468), polyvinylcarbazoles, polythiophenes (for example as described in EP 1028136), polydihydrophenanthrenes (for example as described in WO 05/014689), polyindenofluorenes (for example as described in the applications WO 04/041901 and WO 04/113412), polyketones (for example as described in the unpublished application DE 102004003008.1) or also into copolymers comprising a plurality of these units.

The invention thus furthermore relates to conjugated, partially conjugated and nonconjugated polymers or dendrimers comprising one or more compounds of the formula (1), where one or more bonds of the complex of the formula (1) to the polymer or dendrimer are present.

Furthermore, the metal complexes according to the invention can also be further functionalised and thus converted into extended metal complexes. An example which may be mentioned here is the functionalisation with arylboronic acids by the SUZUKI method or with primary or secondary amines by the HARTWIG-BUCHWALD method.

The above-described complexes according to the invention, or polymers or dendrimers comprising these complexes, are used as active components in electronic components, such as, for example, organic light-emitting diodes (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs) or also organic laser diodes (O-lasers).

Active components are, for example, charge-injection, charge-transport or charge-blocking materials, but in particular emission materials. The compounds according to the invention exhibit particularly good properties for this function, as already explained at the outset and described in greater detail below.

The invention thus furthermore relates to the use of these compounds in electronic components.

The invention furthermore relates to organic electronic components, such as, for example, organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs) or organic laser diodes (O-lasers), but in particular organic light-emitting diodes (OLEDs), comprising one or more complexes of the formula (1). Preference is given to organic electronic components comprising one or more complexes which have part-structures of the formulae (5) to (16), where the above-mentioned preferences for the compounds of the formula (1) also apply to the electronic components.

The compounds are distinguished by the following advantages:

1. In contrast to many metal complexes in accordance with the prior art, which undergo partial or complete pyrolytic decomposition on sublimation, the compounds according to the invention have high thermal stability. This results in a significant increase in the operating lifetime on use in corresponding devices. The high thermal stability of the complexes enables them to be used in a resource-conserving manner.

2. The compounds according to the invention, employed in electroluminescent devices, result in high efficiencies and steep current/voltage curves.

3. The compounds according to the invention have good, in some cases excellent solubility in organic solvents. These materials can thus be purified more easily from solution and they can also be processed from solution by coating or printing techniques. This property is also advantageous in the case of conventional processing by evaporation since cleaning of the plants or the ancillary devices employed, for example shadow masks, is thus considerably simplified.

The present invention is explained in greater detail by the following examples without wishing to restrict it thereto. The person skilled in the art will be able to prepare further complexes according to the invention from the outlines without inventive step or use the process according to the invention.

EXAMPLES

The following syntheses were carried out under a protective-gas atmosphere unless indicated otherwise. The starting materials were purchased from ALDRICH, ABCR (solvents, inorganics, sodium tetrahydridoborate, tri-o-tolylphosphine, 6-chloro-2-pyridinecarboxylic acid), or from Lancaster (pinacolyl pyridine-2-boronate), or from Heraeus (iridium(III)

chloride hydrate). Bis(3-bromobenzyl)ketone was prepared by literature methods (H. Sauriat-Dorizon et al., *J. Org. Chem.* 2003, 68, 240).

Example 1

Synthesis of 1,3-bis(3-bromophenyl)propan-2-ol

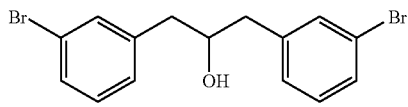

7.6 g (200 mmol) of sodium tetrahydridoborate were added at 0° C. to a solution of 36.8 g (100 mmol) of bis(3-bromobenzyl)ketone in a mixture of 500 ml of THF, 200 ml of isopropanol and 3 ml of acetic acid, and the mixture was stirred at 0° C. for a further 3 h. The ice bath was subsequently removed, and the mixture was stirred at room temperature for a further 12 h. After addition of 300 ml of saturated ammonium chloride solution, the organic phase was separated off, and the aqueous phase was extracted twice with 100 ml of dichloromethane. The combined organic phases were washed once with 500 ml of saturated sodium chloride solution and then freed from the solvent mixture in vacuo, giving 34.9 g (94 mmol), corresponding to 94.3% of theory, of the product in the form of an oil, 97% according to $^1$H-NMR, which were reacted further without purification.

$^1$H-NMR (CDCl$_3$): δ [ppm]=7.31 (d, $^3J_{HH}$=8.0 Hz, 2H, H-4), 7.17 (s, 2H, H-2), 7.11 (dd, $^3J_{HH}$=8.0 Hz, $^3J_{HH}$=8.0 Hz, 2H, H-5), 6.87 (d, $^3J_{HH}$=8.0 Hz, 2H, H-6), 3.88 (m, 1H, CH), 3.10 (m, 4H, CH$_2$), 2.56 (br. s, 1H, OH).

Example 2

Synthesis of 1,3-bis(3-(2-pyridyl)phenyl)propan-2-ol

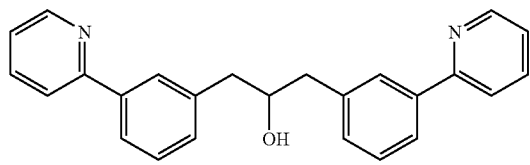

1.64 g (5.4 mmol) of tri-o-tolylphosphine and subsequently 202 mg (0.9 mmol) of palladium(II) acetate were added to a vigorously stirred, degassed suspension of 33.3 g (90 mmol) of 1,3-bis(3-bromophenyl)propan-2-ol, 51.3 g (250 mmol) of pinacolyl-2-pyridylboronate and 40.3 g (380 mmol) of sodium carbonate in a mixture of 500 ml of diethoxyethane, 250 ml of ethanol and 350 ml of water. After the reaction mixture had been heated under reflux for 16 h, the aqueous phase was separated off, and the organic phase was washed with 500 ml of saturated sodium chloride solution and subsequently evaporated to dryness. The oily residue was recrystallised from toluene/acetonitrile, giving 26.0 g (71 mmol) of the product, having a purity of 98% according to $^1$H-NMR, corresponding to a yield of 78.8% of theory, in the form of colourless crystals.

$^1$H-NMR (CDCl$_3$): δ [ppm]=7.76 (m, 4H), 7.61 (m, 4H), 7.35 (dd, $^3J_{HH}$=8.0 Hz, $^3J_{HH}$=8.0 Hz, 2H), 7.20-7.12 (m, 6H), 3.92 (m, 1H, CH), 2.98 (m, 4H, CH$_2$), 2.30 (br. s, 1H, OH).

Example 3

Synthesis of 2-(6-carboxypyridinyl)2-(1,3-bis(3-pyridylphenyl)propyl ether

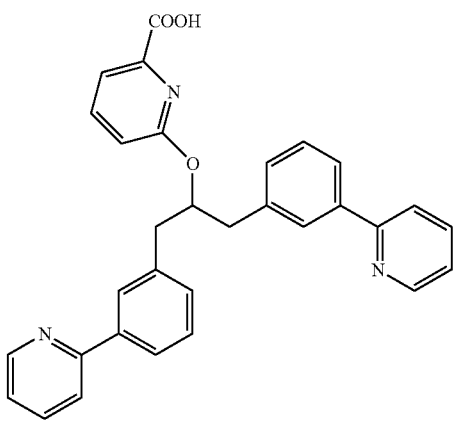

15.8 g (100 mmol) of 6-chloro-2-pyridinecarboxylic acid were added in portions at 0° C. to a suspension of 6.2 g (260 mmol) of sodium hydride in 200 ml of DMSO. When the evolution of hydrogen was complete, a solution of 18.3 g (50 mmol) of 1,3-bis(3-(2-pyridyl)phenyl)propan-2-ol in 50 ml of DMSO was added dropwise to this suspension. When the evolution of hydrogen was complete, the reaction mixture was heated at 135° C. for 60 h. After cooling, the reaction mixture was carefully hydrolysed by addition of 1000 ml of water, adjusted to pH=7 by addition of hydrochloric acid and extracted five times with 200 ml of dichloromethane. The combined organic extracts were washed five times with water. The wax-like solid remaining after removal of the solvent was purified by chromatography (silica gel, dichloromethane: methanol 10:1). The yield, with a purity of 99%, was 9.3 g (19 mmol), corresponding to 38.1% of theory.

$^1$H-NMR (DMSO-d6): δ [ppm]=12.2 (br. s, 1H, COOH), 7.79-7.65 (m, 10H), 7.33-7.26 (m, 3H), 7.14-7.01 (m, 6H), 4.13 (m, 1H, CH), 3.37 (m, 4H, CH$_2$).

Example 4

Synthesis of the Iridium Complex

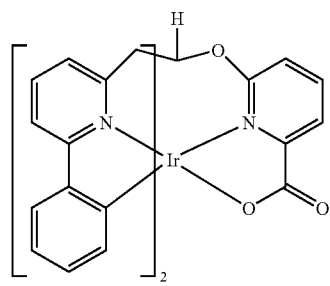

A solution of 2.44 g (5.0 mmol) of 2-(6-carboxypyridinyl) 2-(1,3-bis(3-pyridylphenyl)-propyl ether and 1.76 g (5.0 mmol) of iridium(III) chloride hydrate—calculated as IrCl$_3$×3 H$_2$O—in a mixture of 100 ml of ethoxyethanol and 25 ml of water was heated under reflux for 20 h. After the reaction mixture had been cooled, the yellow, microcrystalline precipitate was filtered off with suction, washed three times with 20 ml of a mixture of ethanol/water (1:1, v:v) and three times with 20 ml of ethanol and then dried. Recrystallisation three times from DMSO gave 2.17 g (3.2 mmol), corresponding to 64.1% of theory, of the product having a purity of >99.8% according to HPLC.

MS (FAB): m/e=677.4.

Example 5

Comparison of the Thermal Stability

The iridium complex described in Example 4 (molecular weight 677.4 g/mol) was sublimed at 340° C. in vacuo. The sublimation proceeded without leaving a residue and with no signs of decomposition, checked by HPLC. Storage experiments at 340° C. for 160 h in sealed ampoules likewise gave no indication of thermally induced decomposition of the iridium complex according to Example 4. By comparison, the analogous, non-polypodal iridium complex in accordance with WO 02/015645 (CAS: 376367-93-0, comparative example in accordance with the prior art, molecular weight=694.7 g/mol) has significantly lower thermal stability, although the introduction of fluorine into the phenylpyridine ligands is claimed to have a positive effect on the thermal stability. The sublimation of this complex, having an initial purity of greater than 99.9% according to $^1$H-NMR and HPLC, at T=340° C. and p=5×10$^{-5}$ mbar gave after 2 h:

about 13% by weight of an iridium-containing ash, about 83% by weight of a yellow sublimate, about 7% by weight of organic condensate, comprising, inter alia, pyridine-2-carboxylic acid, determined by $^1$H-NMR.

The yellow sublimate was not homogeneous. According to $^1$H-NMR and HPLC, it consisted of a mixture. Storage experiments at 340° C. for 160 h resulted in virtually complete decomposition of this complex.

These results show that the iridium complex according to Example 4 according to the invention has excellent long-term stability and is therefore extremely suitable for industrial use. In particular, the long-term temperature stability of the iridium complex according to Example 4 according to the invention is significantly higher than that of the comparative complex in accordance with the prior art.

The complexes according to the invention have comparable or better electroluminescence than complexes in accordance with the prior art.

The invention claimed is:

1. A metal complex of the formula (1)

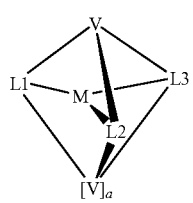

Formula (1)

containing at least one metal M, coordinated to a polypodal ligand L of the formula (2)

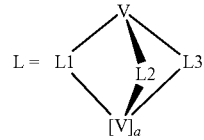

Formula (2)

where V is a bridging unit, containing 1 to 80 atoms from the third, fourth, fifth and/or sixth main group, which covalently bonds the three part-ligands L1, L2 and L3 to one another, and where the index a is equal to 0 or 1, where, in the case a=0, the bridging unit V is omitted;

part-ligand L1 here conforms to the formula (3)

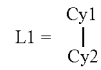

Formula (3)

where Cy1 and Cy2 are substituted or unsubstituted cyclic groups, each of which contains at least one donor atom or C atom in the ring or bonded exocyclically via which the cyclic group is bonded to the metal; the groups Cy1 and Cy2 are bonded to one another via a covalent bond or a common edge and are optionally linked to one another via substituents and thus form a polycyclic, aliphatic or aromatic ring system;

part-ligand L2 is a donor ligand, containing one or more donor atoms and 2 to 40 C atoms, with the proviso that part-ligand L2 is not built up from two rings or part-rings which are both bonded to the metal;

part-ligand L3 is identical to or different from part-ligand L1 or part-ligand L2 and the metal complex is electrically neutral.

2. The metal complex according to claim 1, wherein the cyclic groups Cy1 and Cy2 are aromatic.

3. The metal complex according to claim 1, wherein the sum of the valence electrons around the metal atom is 18.

4. The metal complex according to claim 1, wherein Cy1 is not equal to Cy2, and one of the two rings is bonded to the metal via a metal-carbon bond and the other via a donor atom other than carbon.

5. The metal complex according to claim 1, wherein the bridging unit V has 1 to 80 atoms from main group 3, 4, 5 and/or 6 or a 3- to 6-membered homo- or heterocycle.

6. The metal complex according to claim 1, wherein part-ligand L2 is a bidentate-chelating ligand having two donor atoms.

7. The metal complex according to claim 1, wherein the ligand L has a structure of the formula (4):

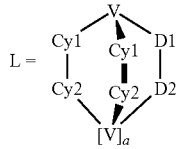

Formula (4)

where the symbols D1 and D2, in each case identically or differently, stand for donor groups, each containing one donor atom.

8. The metal complex according to claim 1, wherein part-ligand L1 together with the metal M and the bridging unit V has a part-structure of the formulae (5) to (16):

Formula (5)
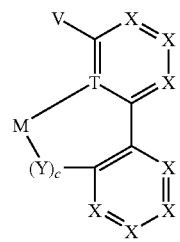

Formula (6)
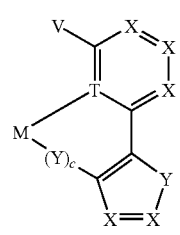

Formula (7)
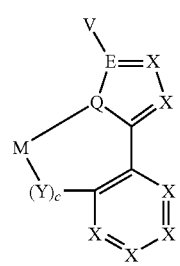

Formula (8)
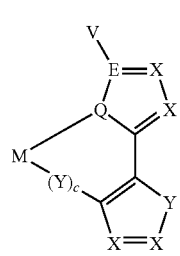

Formula (9)
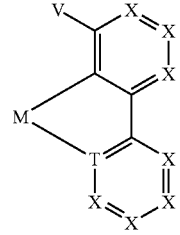

Formula (10)
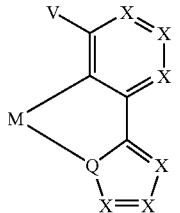

Formula (11)
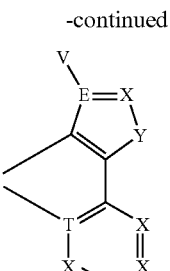

Formula (12)
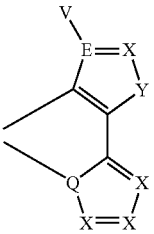

Formula (13)
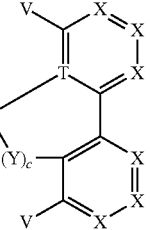

Formula (14)
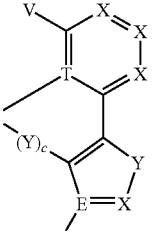

Formula (15)
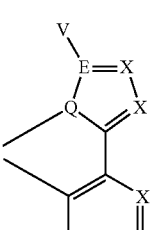

Formula (16)
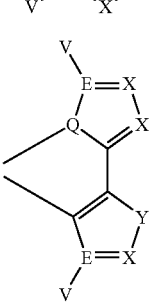

where the symbols and indices have the following meaning:

M is, identically or differently on each occurrence, a transition metal;

E is, identically or differently on each occurrence, C, N or P;

Q is, identically or differently on each occurrence, O, S, Se, Te or N;

T is, identically or differently on each occurrence, N, P or C;

X is, identically or differently on each occurrence, CR, N or P;

Y is, identically or differently on each occurrence, $NR^1$, O, S, Se, Te, SO, SeO, TeO, $SO_2$, $SeO_2$, $TeO_2$, $R^1SO$, $R^1SeO$, $R^1TeO$, $R^1SO_2$, $R^1SeO_2$, $R^1TeO_2$, $R^1PO$ or $(R^1)_2PO$;

V is, identically or differently on each occurrence, B, $BR^-$, $B(CR_2)_3$, $RB(CR_2)_3^-$, $B(O)_3$, $RB(O)_3^-$, $B(CR_2CR_2)_3$, $RB(CR_2CR_2)_3^-$, $B(CR_2O)_3$, $RB(CR_2O)_3^-$, $B(OCR_2)_3$, $RB(OCR_2)_3^-$, $Al(O)_3$, $RAl(O)_3^-$, $Al(OCR_2)_3$, $RAl(OCR_2)_3^-$, CR, $CO^-$, $CN(R^1)_2$, $RC(CR_2)_3$, $RC(O)_3$, $RC(CR_2CR_2)_3$, $RC(CR_2O)_3$, $RC(OCR_2)_3$, $RC(SiR_2)_3$, $RC(SiR_2CR_2)_3$, $RC(CR_2SiR_2)_3$, $RC(SiR_2SiR_2)_3$, SiR, $RSi(CR_2)_3$, $RSi(O)_3$, $RSi(CR_2CR_2)_3$, $RSi(OCR_2)_3$, $RSi(CR_2O)_3$, $RSi(SiR_2)_3$, $RSi(SiR_2CR_2)_3$, $RSi(CR_2SiR_2)_3$, $RSi(SiR_2SiR_2)_3$, N, NO, $NR^+$, $N(CR_2)_3$, $RN(CR_2)_3^+$, $N(C=O)_3$, $N(CR_2CR_2)_3$, $RN(CR_2CR_2)^+$, P, PO, PS, PSe, PTe, $P(O)_3$, $PO(O)_3$, $P(OCR_2)_3$, $PO(OCR_2)_3$, $P(CR_2)_3$, $PO(CR_2)_3$, $P(CR_2CR_2)_3$, $PO(CR_2CR_2)_3$, As, AsO, AsS, AsSe, AsTe, $As(O)_3$, $AsO(O)_3$, $As(OCR_2)_3$, $AsO(OCR_2)_3$, $As(CR_2)_3$, $AsO(CR_2)_3$, $As(CR_2CR_2)_3$, $AsO(CR_2CR_2)_3$, Sb, SbO, SbS, SbSe, SbTe, $Sb(O)_3$, $SbO(O)_3$, $Sb(OCR_2)_3$, $SbO(OCR_2)_3$, $Sb(CR_2)_3$, $SbO(CR_2)_3$, $Sb(CR_2CR_2)_3$, $SbO(CR_2CR_2)_3$, Bi, BiO, BiS, BiSe, BiTe, $Bi(O)_3$, $BiO(O)_3$, $Bi(OCR_2)_3$, $BiO(OCR_2)_3$, $Bi(CR_2)_3$, $BiO(CR_2)_3$, $Bi(CR_2CR_2)_3$, $BiO(CR_2CR_2)_3$, $S^+$, $S(CR_2)_3^+$, $S(CR_2CR_2)_3^+$, $Se^+$, $Se(CR_2)_3^+$, $Se(CR_2CR_2)_3^+$, $Te^{30}$, $Te(CR_2)_3^+$, $Te(CR_2CR_2)_3^+$ or corresponding asymmetrical analogues; or a unit of the formula (17) or formula (18)

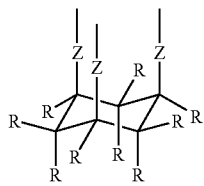

Formula (17)

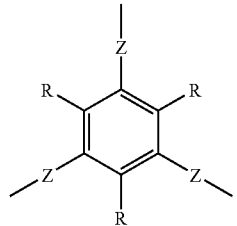

Formula (18)

Z is on each occurrence, identically or differently, a divalent group $CR_2$, NR, O, S, $SiR_2$, PR, $CR_2$—$CR_2$, $CR_2$—NR, $CR_2$—O, $CR_2$—S, $CR_2$—$SiR_2$ or $CR_2$—PR;

R is, identically or differently on each occurrence, H, F, Cl, Br, I, $NO_2$, CN, a straight-chain, branched or cyclic alkyl or alkoxy group having 1 to 20 C atoms, in which one or more non-adjacent $CH_2$ groups is optionally replaced by —$R^1C$=$CR^1$—, —C≡C—, $Si(R^1)_2$, $Ge(R^1)_2$, $Sn(R^1)_2$, C=O, C=S, C=Se, C=$NR^1$, —O—, —S—, —$NR^1$— or —$CONR^1$— and in which one or more H atoms is optionally replaced by F, or an aryl, aryloxy or heteroaryl group having 1 to 14 C atoms, which optionally is substituted by one or more non-aromatic radicals R, or a diarylamino group having 6 to 20 C atoms; which is optionally substituted by one or more non-aromatic radicals R; a plurality of substituents R here, both on the same ring and also on the two different rings, may together in turn form a further mono- or polycyclic, aliphatic, aromatic and/or benzo-fused ring system;

$R^1$ is, identically or differently on each occurrence, H or an aliphatic or aromatic hydrocarbon radical having 1 to 20 C atoms;

c is, identically or differently on each occurrence, 0 or 1.

9. The metal complex according to claim 8, wherein M on each occurrence, identically or differently, stands for a transition-metal ion having an atomic number of greater than 38.

10. The metal complex according to claim 8, wherein Q on each occurrence, identically or differently, stands for O, S or N.

11. The metal complex according to claim 8, wherein E on each occurrence, identically or differently, stands for C or N.

12. The metal complex according to claim 8, wherein T on each occurrence, identically or differently, stands for N or P.

13. The metal complex according to claim 8, wherein X on each occurrence, identically or differently, stands for CR or N.

14. The metal complex according to claim 8, wherein V on each occurrence, identically or differently, stands for B, $BR^-$, $B(CR_2)_3$, $RB(CR_2)_3^-$, $B(O)_3$, $RB(O)_3^-$, $B(CR_2CR_2)_3$, $B(OCR_2)_3$, $RB(OCR_2)_3^-$, CR, $CNR^1_2$, $RC(CR_2)_3$, $RC(O)_3$, $RC(CR_2CR_2)_3$, $RC(CR_2O)_3$, $RC(OCR_2)_3$, SiR, $RSi(CR_2)_3$, $RSi(O)_3$, $RSi(CR_2CR_2)_3$, $RSi(OCR_2)_3$, $RSi(CR_2O)_3$, N, $NR^+$, $N(CR_2)_3$, $RN(CR_2)_3^+$, $N(C=O)_3$, $N(CR_2CR_2)_3$, $RN(CR_2CR_2)^+$, P, PO, $P(O)_3$, $PO(O)_3$, $P(OCR_2)_3$, $PO(OCR_2)_3$, $S^+$, $S(CR_2)_3^+$, $S(CR_2CR_2)_3^+$ or corresponding asymmetrical analogues or a group of the formula (17) or formula (18).

15. The metal complex according to claim 8, wherein Z on each occurrence, identically or differently, stands for a divalent group $CR_2$, NR, O, S, $SiR_2$ or PR.

16. The metal complex according to claim 8, wherein Y on each occurrence, identically or differently, stands for O, S or $NR^1$.

17. The metal complex according to claim 8, wherein R on each occurrence, identically or differently, stands for H, F, Cl, Br, I, CN, a straight-chain, branched or cyclic alkyl or alkoxy group having 1 to 6 C atoms or an aryl, aryloxy or heteroaryl group having 3 to 8 C atoms, which optionally is substituted by one or more non-aromatic radicals R, or a diarylamino group having 8 to 12 C atoms, which optionally is substituted by one or more non-aromatic radicals R; two or more substituents R here, both on the same ring and also on the two different rings, may together in turn form a further mono- or polycyclic, aliphatic, aromatic and/or benzo-fused ring system.

18. The metal complex according to claim 8, wherein c on each occurrence is equal to 0.

19. The metal complex according to claim 1, wherein the part-ligands L2 are bidentate-chelating ligands which have two donor groups D1 and D2, where the donor atoms are selected from main groups 5 and 6 or represent isonitrile groups, but otherwise do not have any direct metal-carbon bonds; the donor groups D1 and D2 here cannot both represent cyclic systems which are both bonded to the metal.

20. The metal complex according to claim 19, wherein the donor atoms of donor groups D1 and D2 are nitrogen, phosphorus, oxygen or sulfur.

21. The metal complex according to claim 20, wherein the donor groups D1 and D2 are aromatic nitrogen heterocycles, aliphatic amines, aliphatic cyclic amines, nitriles, amides, imides, imines, alkyl-, aryl- or mixed alkylarylphosphines, alkyl-, aryl- or mixed alkylarylphosphine halides, alkyl, aryl or mixed alkyl aryl phosphites, phosphaaromatics, alcohols, alcoholates, open-chain or cyclic ethers, carbonyl groups, phosphine oxide groups, sulfoxide groups, carboxylates, phenols, phenolates, oximes, hydroxamates, β-ketoketonates, β-ketoesters, β-diesters, aliphatic or aromatic thiols and thiolates, open-chain or cyclic thioethers, thiophene, thiocarbonyl groups, phosphine sulfides or thiocarboxylates, each of which optionally is substituted by groups R or unsubstituted.

22. The metal complex according to claim 21, wherein the part-ligands L2 are β-ketoketonates, β-ketoesters, β-diesters, pyridylcarboxylates, α-amino acids, iminoacetoacetonates, hydroxamates, diphosphines, pyridylphosphines, α-phosphinocarboxylates, glycol ethers, ether alcoholates, diamines, imines, diimines, carboxylates derived from aminocarboxylic acids, salicyliminates, dialcoholates, dithiolates, each of which are substituted by R or unsubstituted.

23. A ligand L of the formula (2)

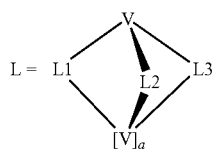

Formula (2)

where V is a bridging unit, containing 1 to 80 atoms from the third, fourth, fifth and/or sixth main group, which covalently bonds the three part-ligands L1, L2 and L3 to one another, and where the index a is equal to 0 or 1, where, in the case a=0, the bridging unit V is omitted;

part-ligand L1 here conforms to the formula (3)

Formula (3)

where Cy1 and Cy2 are substituted or unsubstituted cyclic groups, each of which contains at least one donor atom or C atom in the ring or bonded exocyclically via which the cyclic group is bonded to the metal; the groups Cy1 and Cy2 are bonded to one another via a covalent bond or a common edge and are optionally linked to one another via substituents and thus form a polycyclic, aliphatic or aromatic ring system;

part-ligand L2 is a donor ligand, containing one or more donor atoms and 2 to 40 C atoms, with the proviso that part-ligand L2 is not built up from two rings or part-rings which are both bonded to the metal;

part-ligand L3 is identical to or different from part-ligand L1

24. A process for the preparation of a complex of the formula (1)

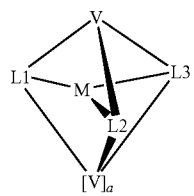

Formula (1)

which comprises reacting the ligand of the formula (2)

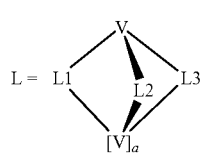

Formula (2)

where V is a bridging unit, containing 1 to 80 atoms from the third, fourth, fifth and/or sixth main group, which covalently bonds the three part-ligands L1, L2 and L3 to one another, and where the index a is equal to 0 or 1, where, in the case a=0, the bridging unit V is omitted;

part-ligand L1 here conforms to the formula (3)

Formula (3)

where Cy1 and Cy2 are substituted or unsubstituted cyclic groups, each of which contains at least one donor atom or C atom in the ring or bonded exocyclically via which the cyclic group is bonded to the metal; the groups Cy1 and Cy2 are bonded to one another via a covalent bond or a common edge and are optionally linked to one another via substituents and thus form a polycyclic, aliphatic or aromatic ring system;

part-ligand L2 is a donor ligand, containing one or more donor atoms and 2 to 40 C atoms, with the proviso that part-ligand L2 is not built up from two rings or part-rings which are both bonded to the metal;

part-ligand L3 is identical to or different from part-ligand L1 or part-ligand L2;

or precursors of this ligand with metal alcoholates of the formula (19), with metal ketoketonates of the formula (20) or metal halides of the formula (21)

$M(OR^1)_p$

Formula (19)

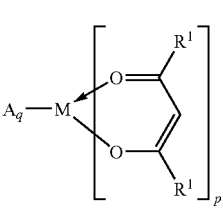

Formula (20)

$MHal_p$

Formula (21)

where the following applies to the symbols and indices:
  M is on each occurrence, identically or differently, a transition-metal ion;
  Hal is on each occurrence, identically or differently, F, Cl, Br or I;
  A is on each occurrence, identically or differently, a neutral or monoanionic, monodentate or bidentate ligand,
  p is on each occurrence, identically or differently, 1, 2, 3, 4 or 5, where p in formulae (19) and (21) indicates the valence of the metal M;
  q is on each occurrence, identically or differently, 0, 1, 2, 3 or 4;
  the compound of the formula (20) here may also be charged and also contain a counterion; and
  $R^1$ is, identically or differently on each occurrence, H or an aliphatic or aromatic hydrocarbon radical having 1 to 20 C atoms.

25. The process according to claim 24, wherein the reaction is activated thermally, photochemically or by microwave radiation.

26. The process according to claim 24, wherein the ligand of the formula (2) is reacted with metal compounds of the formulae (19), (20) and (21):

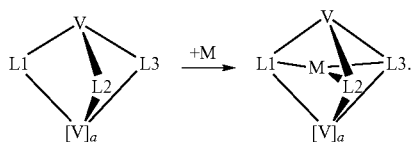

27. The process according to claim 24, wherein a polypodal precursor of the cryptand is employed in the complexing step, and the second bridging unit V is introduced in a second synthetic step:

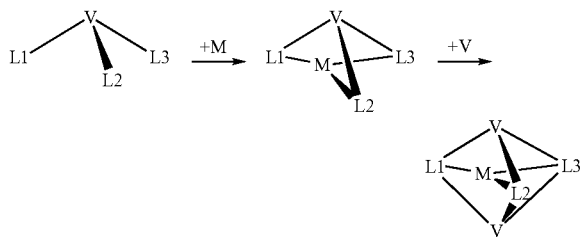

or in that a simple precursor of the ligand is employed, and all bridging units V are formed in a further step:

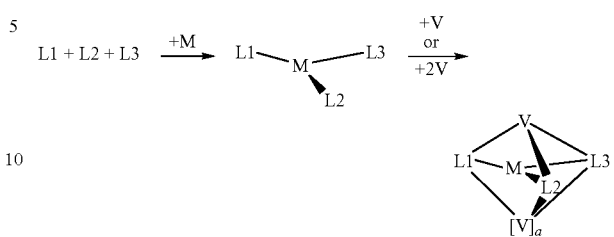

or in that a simple or macrocyclic precursor of the ligand is employed, and the third part-ligand is introduced and linked to the bridging units V:

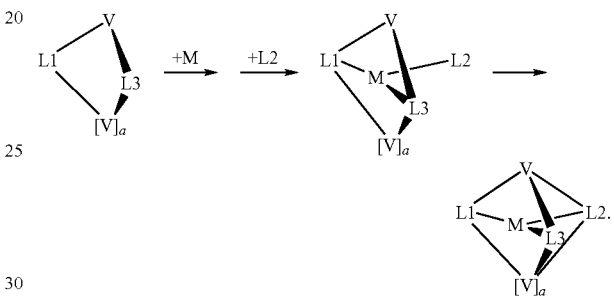

28. A conjugated, partially conjugated and non-conjugated polymer or dendrimer comprising one or more complex according to claim 1, where one or more bonds of the complex to the polymer or dendrimer are present.

29. An organic electronic component comprising one or more complexes according to claim 1.

30. The organic electronic component according to claim 29, wherein the component is organic light-emitting diode (OLED), organic integrated circuit (O-IC), organic field-effect transistor (O-FET), organic thin-film transistor (O-TFT), organic light-emitting transistor (O-LET), organic solar cell (O-SC), organic optical detector, organic photoreceptor, organic field-quench device (O-FQD) or organic laser diode (O-laser).

* * * * *